United States Patent
Borazjani et al.

(10) Patent No.: US 10,582,993 B2
(45) Date of Patent: Mar. 10, 2020

(54) SMART SURGICAL SPACER FOR TISSUE-IMPLANT INTERFACE

(71) Applicant: COSM Medical, Toronto (CA)

(72) Inventors: Ali Borazjani, Cleveland, OH (US); Benjamin C Weed, Starkville, MS (US)

(73) Assignee: COSM Medical, Toronto, Ontario (CA)

( * ) Notice: Subject to any disclaimer, the term of this patent is extended or adjusted under 35 U.S.C. 154(b) by 123 days.

(21) Appl. No.: 15/503,670

(22) PCT Filed: Aug. 13, 2015

(86) PCT No.: PCT/US2015/045131
§ 371 (c)(1),
(2) Date: Feb. 13, 2017

(87) PCT Pub. No.: WO2016/025757
PCT Pub. Date: Feb. 18, 2016

(65) Prior Publication Data
US 2017/0265980 A1  Sep. 21, 2017

Related U.S. Application Data

(60) Provisional application No. 62/036,986, filed on Aug. 13, 2014.

(51) Int. Cl.
*A61F 2/00* (2006.01)
*A61B 90/00* (2016.01)
*A61B 17/00* (2006.01)

(52) U.S. Cl.
CPC ............ *A61F 2/0045* (2013.01); *A61B 90/06* (2016.02); *A61B 2017/00115* (2013.01); *A61B 2017/00424* (2013.01); *A61B 2017/00725* (2013.01); *A61B 2090/064* (2016.02); *A61B 2505/05* (2013.01); *A61B 2560/0238* (2013.01); *A61F 2240/008* (2013.01)

(58) Field of Classification Search
CPC .............. A61B 2090/064; A61B 90/06; A61B 2017/00115; A61B 2017/00424; A61B 2560/0238; A61B 2505/05; A61B 2017/00725; A61F 2/0045
USPC ........................ 600/29–31, 37; 128/897–899
See application file for complete search history.

(56) References Cited

U.S. PATENT DOCUMENTS

| | | | | |
|---|---|---|---|---|
| 5,836,894 A * | 11/1998 | Sarvazyan | ........... | A61B 1/0052 600/587 |
| 6,050,937 A * | 4/2000 | Benderev | ............. | A61F 2/0036 600/30 |
| 6,272,371 B1 * | 8/2001 | Shlomo | ................. | A61B 34/20 128/899 |
| 6,302,840 B1 * | 10/2001 | Benderev | ............. | A61F 2/0036 600/37 |
| 6,584,856 B1 * | 7/2003 | Biter | ........................ | G01B 7/24 73/768 |

(Continued)

OTHER PUBLICATIONS

English Machine Translation of Foreign Patent RU2464925 C2, SENSIMED AG, Oct. 27, 2014 (see attached PDF format document titled 15503670EnglishTranslationRU2464925C2_NPL_Nov16_2018).*

Primary Examiner — Navin Natnithithadha
Assistant Examiner — Sunita Reddy
(74) Attorney, Agent, or Firm — Rosenberg, Klein & Lee (57) ABSTRACT

A surgical spacer equipped to measure important parameters for determining the optimal placement of a surgically-implanted sling.

22 Claims, 11 Drawing Sheets

(56) References Cited

U.S. PATENT DOCUMENTS

| | | | |
|---|---|---|---|
| 2004/0073235 A1* | 4/2004 | Lund | A61B 17/1227 606/151 |
| 2004/0116944 A1* | 6/2004 | Chu | A61F 2/0045 606/151 |
| 2007/0106114 A1* | 5/2007 | Sugimoto | A61B 1/31 600/117 |
| 2007/0191829 A1* | 8/2007 | McGee | A61B 18/14 606/41 |
| 2009/0138007 A1* | 5/2009 | Govari | A61B 1/0008 606/33 |
| 2009/0306650 A1* | 12/2009 | Govari | A61B 18/1492 606/41 |
| 2010/0160770 A1* | 6/2010 | Govari | A61B 5/06 600/424 |
| 2012/0004576 A1* | 1/2012 | Govari | A61M 25/0068 600/587 |
| 2012/0149966 A1* | 6/2012 | Ludwin | A61B 5/065 600/11 |
| 2012/0149967 A1* | 6/2012 | Ludwin | A61B 18/1492 600/11 |
| 2012/0150075 A1* | 6/2012 | Ludwin | A61B 5/065 600/587 |
| 2012/0253167 A1* | 10/2012 | Bonyak | A61B 5/6885 600/409 |
| 2013/0218163 A1* | 8/2013 | Frey | A61B 5/0488 606/87 |
| 2015/0133726 A1* | 5/2015 | Lowman | A61F 2/0045 600/30 |
| 2017/0105803 A1* | 4/2017 | Wong | A61B 34/30 |

* cited by examiner

SMART SURGICAL SPACER FOR TISSUE-IMPLANT INTERFACE

PRIORITY CLAIM

This application is a continuation of and claims priority to and the full benefit of PCT patent application PCT/US2015/045131 filed on Aug. 13, 2015, which claims priority to and the full benefit of U.S. provisional application No. 62/036,986 entitled "Sensor for Tissue-Implant Interface" filed Aug. 13, 2014. The present application also incorporates U.S. provisional application No. 62/036,986 in its entirety.

TECHNICAL FIELD

The field is the tensioning of sub-urethral slings used to treat female or male stress urinary incontinence (SUI) or any other implantable sling or device.

DETAILED DESCRIPTION

Sub-urethral slings are effective at alleviating SUI symptoms, and are one of the least invasive surgical treatments available to the pelvic surgeon. Nonetheless, these procedures are affected by complications including urinary retention, pelvic pain, and vaginal extrusion/erosion and urethral extrusion/erosion; and some patients may not see a large enough reduction in SUI symptoms to improve their quality of life. Proper tensioning of the sling is crucial in avoiding complications and surgical revisions, as well as ensuring the patient sees symptomatic improvement commensurate with a surgical intervention.

A device and method are provided to enable surgeons to measure and adjust mechanical loads on a sling for relieving SUI, or on an implanted device of any kind. As used throughout this specification, a "sling" includes not only a sling for SUI, but also any other implanted device.

During sub-urethral sling surgery a graft (synthetic, autologous, cadaveric, or biological xenograft) is positioned below the urethra to provide additional support. Excessive urethral movements, or hypermobility, may lead to SUI. Therefore it is important that the implanted sling provide adequate support by being placed against the posterior of the urethra. If too much tension is applied to the sling during placement, complications including urinary outlet obstruction may follow. However, if the sling is too loose, then the patient may suffer persistent SUI. Typically, once the sling is guided through the suprapubic, retropubic, or obturator tissues and appropriately positioned, the surgeon will use a blunt instrument which is readily available in the surgical field as a spacer between the sling and urethra while applying tension to the distal ends of the sling. Tension is applied until the surgeon feels the sling will provide the needed support to the urethra without causing obstruction or other complications. The spacer comprises a self-contained, stand-alone tool for use for spacing and for measuring the mechanical load applied by the sling to the spacer and displaying the load in real time on a small display, such as a liquid crystal display (LCD), a multi-colored light emitting diode, an array of light emitting diodes, or a light emitting diode display. Moreover, since the tool functions as both a spacer and a load sensor, there is no need to remove the tool to adjust the sling and then re-measure the tension. Instead, the tool can be used as a lever to assist with sling adjustment while simultaneously measuring loads. In addition to measuring the load imparted by the sling onto the spacer, the spacer is capable of detecting changes in the angle of the urethra as well. Using the data regarding the load on the display, the surgeon can observe and adjust the sling accordingly.

BRIEF DESCRIPTION OF THE DRAWINGS

FIG. 1-A is a perspective view of a first embodiment of a surgical spacer for measuring tension on a sub-urethral sling.

FIG. 1-B is an enlargement of the side view of the flex-beam in the first embodiment in FIG. 1-A.

FIG. 1-C depicts a surgeon using the first embodiment with the flex-beam inserted between the sling and bodily tissue.

FIG. 1-D is a side view of the first embodiment showing Bending Load A from the surgeon's manipulation of the handle, Bending Load B from the sling, and Bending Load C from the tissue.

FIG. 1-E is a cutaway of the first embodiment showing the forces when Bending Load B is applied to the sensing region and the strain gauges.

FIG. 2-A is a side view of a second embodiment of the surgical spacer wherein the flex-beam comprises a slot.

FIG. 2-B is a cross section of the slot at line A-A shown in FIG. 2-A.

FIG. 2-C is a cutaway of the second embodiment showing the forces when Bending Load B is applied to the sensing region comprising a slot and the strain gauges.

FIG. 6-A is a side view of an additional embodiment, including a cutaway section of the probe holder which is cradling a probe, and also of the sensor for measuring angle and mobility of a bodily cavity during Valsalva or Crede maneuvers.

FIG. 6-B is a top view of the embodiment with the probe holder and the sensor for angle and mobility.

The present invention comprises a smart surgical spacer 1 which is placed between the sling and bodily tissue during surgery. The surgical spacer is used as a lever to adjust the sling and to ensure there is some slack or decreased tension within the sling once the spacer is removed. If the surgeon desires a low tension or tension-free placement of the sling, then it is preferred that, once the spacer is removed, the sling barely touches the urethra and does not impart significant force on it. The present invention also comprises a method for measuring the load the sling exerts on the spacer rather than directly measuring the load on the bodily tissue itself. As such, the load that the sling will exert on the bodily tissue will be less than the load measured when the spacer is between the body tissue and the sling.

Without limitation and by way of illustration only, the spacer and method disclosed herein are useful in measuring mechanical loads from a sub-urethral sling on the spacer during surgery for the treatment of SUI, particularly mid-urethral sling procedures.

The load from the sling onto the sensing region 6 will result in microscopic expansion and/or contraction of the sensing region. As a result, the strain gauges, which are bonded to the sensing region, will expand and/or contract with the sensing region. The expansion and contraction of the strain gauges results in changes in the electrical properties of the strain gauge which are proportional to the degree of expansion and/or contraction. Once the spacer is removed from between the tissue (e.g., the urethra) and the sling, the load between the sling and the tissue is less than what was initially measured. For example, initially the device is in place above the sling as the sling is being tensioned. Given that, in one embodiment, the device also functions as a spacer with a thickness of 5-7 mm, the load measurements obtained correspond to the load applied on the sling when only the device is in place above the sling. Once the device is removed, the sling collapses into the 5-7 mm void that was once occupied by the sensing region 6 of the spacer. Therefore, the load measurements obtained during the time of sling placement are only associated with the load between the tissue and the sling once the device is removed. This end load will be significantly smaller than the load measured with the sling in place, and it is not a function of the device to measure directly the end load of the sling on the body tissue. However, the measurements obtained with the spacer in place (i.e. between the sling and urethra) may be correlated to the end load that the sling places on the urethra following removal of the spacer.

A strain gauge is one of several types of mechanical load transducers which detect bending loads. The mechanical load transducers which may be used in the present invention may be selected from the group consisting of strain gauges, standard load transducers, pressure-sensitive-conductive rubbers, piezoelectric force transducers and the like.

Figure 1:
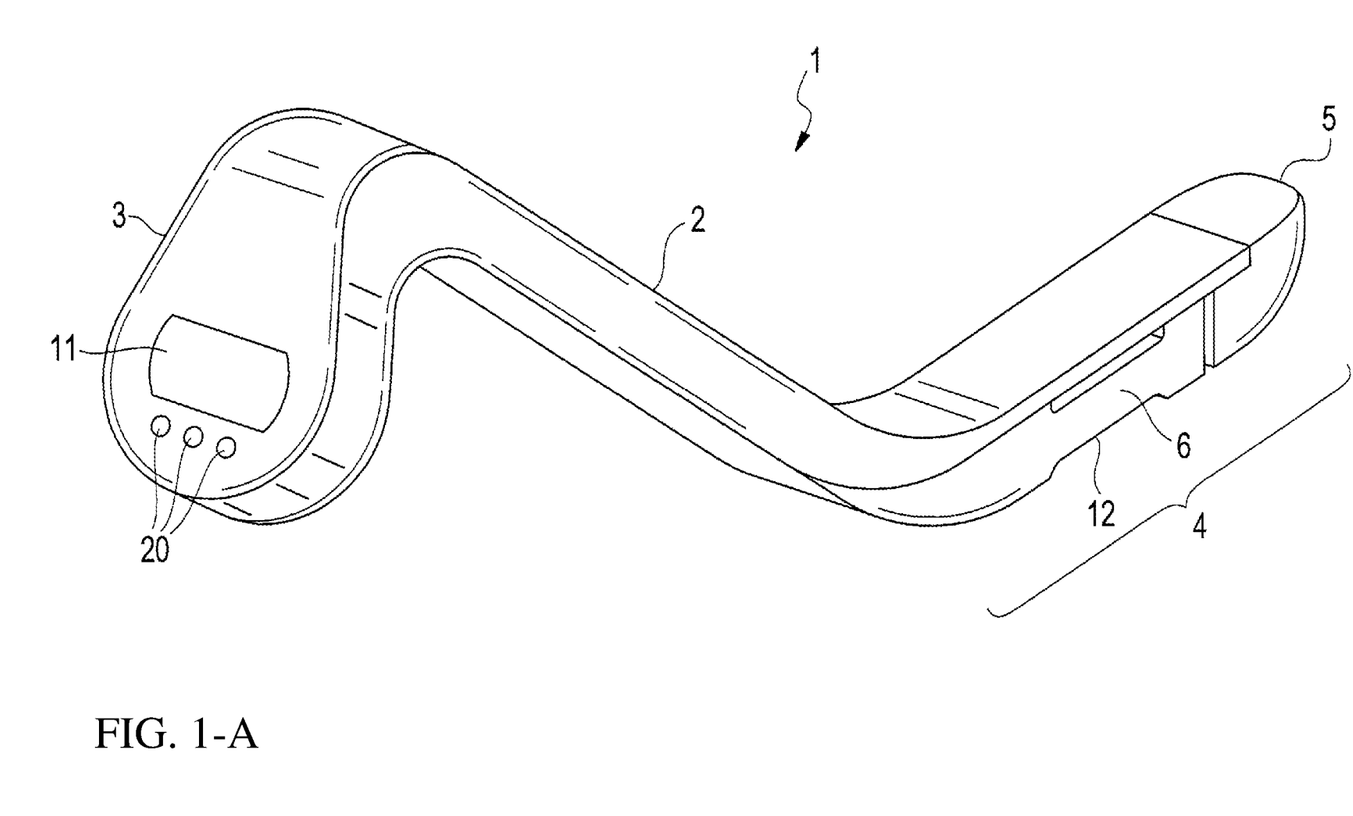

As seen in FIG. 1-A, a first embodiment of the spacer 1 comprises a shaft 2 connected to a handle 3 near the proximal end of the shaft and a flex-beam 4 connected to the shaft 2 near its distal end. The flex-beam 4 comprises a tip 5 and a sensing region 6 which comprises one or more strain gauges to measure strain on the sensing region of the flex-beam which is in contact with a sling 14. More specifically, the strain gauge measures how the sensing region 6 bends in response to loading from the sling. The voltage output of the one or more strain gauge circuits is correlated to the degree of bending of the sensing region 6, and thus the load placed on the sensing region. In one embodiment, the flex-beam 4 and the handle 3 attach to the shaft 2 by any mechanical means such as screws and pins or other anchors (adhesives, nut/bolt, press-fit rivet, and the like). In another embodiment, shaft 2, the handle 3 and flex-beam 4 are formed together as one piece and are integral to one another.

The spacer 1 allows for the sensing region 6 to interface with patient tissues 13 and sling 14 to measure loading, and the shaft 2 and handle 3 allow the surgeon to hold and position the flex-beam. Additionally, the materials used for the shaft, in one embodiment preferably steel, are strong enough to allow for the device to function as a lever for adjusting the sling. The handle, in one embodiment, includes a display 11 which displays the measurements to inform and assist the surgeon with performing the surgery. Together, the handle and shaft are designed in a way to ergonomically support the thumb and fingers while optimizing device functionality.

FIG. 1-B is an enlargement from FIG. 1-A of the flex-beam 4 comprising the sensing region 6 showing that its thickness is narrower than the flex-beam 4 as a whole. In this embodiment, the flex-beam is attached to a paddle 10 made of a strong material such as steel. The paddle may be a flattened portion of the tube which comprises the shaft 2. One pair of strain gauges is positioned on a mounting area on the top 7 of the sensing region 6 and another pair of strain gauges is positioned on a mounting area on the bottom 8. A gap 9 isolates any bending load near the tip 5 from the bending load on the sensing region 6. In one embodiment, the flex-beam is covered with thin heat-shrink tubing (not depicted) such that water-sensitive components of the device will be protected from moisture, while still allowing the device to sense loads. Additionally, in a reusable embodiment of the spacer, this tubing will seal the junctions between the various components, which will enable the device to be more easily cleaned and/or sterilized following use.

Preferably, the sensing region 6 is mechanically isolated from the rounded tip 5 via a gap 9 and the use of a pin (not depicted) at the portion of the flex-beam on the proximal side of the gap 9. The pin allows the sensing region to move perpendicularly to the paddle 10, but not side to side. The proximal end of the flex beam (closest to the shaft) is attached securely to the paddle or the shaft, but the most distal end of the flex-beam (and proximal to the gap 9) is either pinned or is not attached in any way. The flex-beam 4 comprises a sensing region 6 which flexes or bends (microscopically) during the tensioning of the sling. This bending alters the electrical properties of the at least one strain gauge 15, 16, 17, 18 whose output is communicated to the display. The sensing region is one alternative for providing a convenient location for isolating the load from the sling, because the design of the flex-beam at this region creates relative weakness in the probe, and so bending of the probe will be greatest in the sensing region. In one embodiment the sensing region is solid but is narrower than the rest of the flex-beam which helps further isolate the load from the sling because the narrowing creates relative weakness in the sensing region, and so bending of the flex-beam from the sling will be greatest at this region. In one embodiment the sensing region may be further comprised of a curve 12 where the sling is positioned. This curve serves to ensure consistent readings by providing the surgeon with haptic and visual feedback that the sling is located at the location where the strain gauges are mounted. The curve 12 provides a nesting place for the sling and also prevents the sling from contacting the strain gauges 17-18 on the bottom. Similarly, a wall 26 near each side of the top of the sensing region prevents the paddle 10 from contacting the strain gauges 15, 16 directly. In one embodiment with two pairs of strain gauges 15-16, 17-18 are placed near the center of the sensing region 6 to maximize the sensitivity of the measurements they create. In one embodiment with two pairs of strain gauges, the strain gauges 15-16, 17-18 are placed between walls 26 which are adjacent to both sides of the top 7 and bottom 8 of the sensing region and help protect the strain gauges. The strain gauges on the bottom 8 of the sensing region 6 are located between curves 12 on both sides of the sensing region 6. The walls 26 and the curves 12 allow the strain gauges to sense the deformation of the sensing region while being isolated from contact with the sling, surgeon, or tissue; which might alter the measurements or otherwise affect the strain gauges. These walls 26 and curves 12 further include one or more small posts 25 which allow the sensing region to bend upward but prevent excessive bending which could damage the sensing region and the strain gauges. This functions to protect the strain gauges from over-straining and to increase the durability of the instrument.

Strain gauges may be located in any number and any combination in any location in or near the sensing region 6. Generally speaking, in any embodiment of the spacer, the more strain gauges in or near the sensing region 6 the more sensitive the measurements will be.

Figure 2:
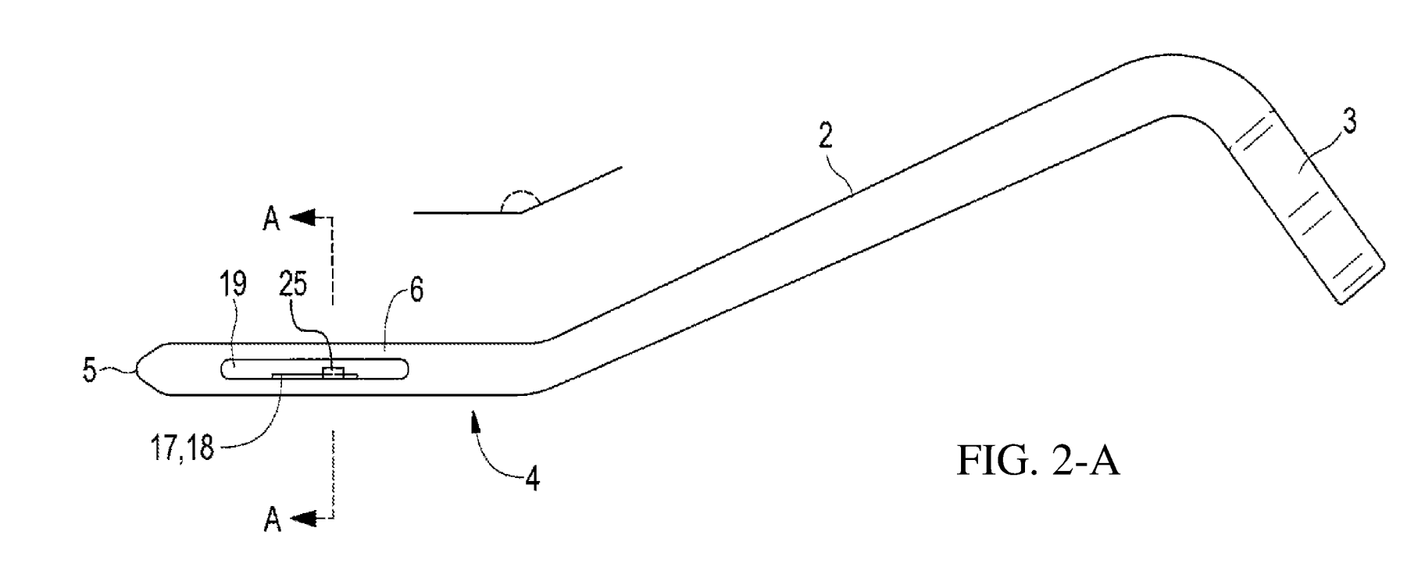

In one embodiment, the tip region 5 may be about 15 mm in length. In one embodiment, the first 5 cm from the tip may have a clamshell shape, i.e., a concave top part which is a urethral groove 28 and a convex bottom, as shown in FIG. 2-B). The instrument is advanced until the sling lies over the sensing region 6, which is contained within the flex-beam and, in one embodiment, measures about 20 mm in length and begins after the tip region. The sensing region allows for enhanced consistency between different load readings by enabling the surgeon to advance the instrument to approximately the same region each time. The concavity of the urethral groove 28 allows for enhanced stabilization with urethra, and the urethral groove may be used with any embodiment of the spacer. The convexity (or only slight convexity, or nearly flat) feature of the bottom of the sensing region (as shown in FIG. 2-B) allows for even distribution of load from the sling. The shapes of the top and bottom part reduce the potential of artifactual readings due to rotation of the device (clockwise or anticlockwise with respect to the longitudinal axis of the device). Overall, these features function to increase reproducibility of measurements.

The handle 3 is ergonomically-optimized for handling, control, and visibility during sling placement. The angle between the flex-beam and the handle allows for easy visibility of the sling during placement and decreases the effect of bending moment artifact on load measurements.

As shown in FIG. 1-C, the spacer is designed to be placed between a patient's periurethral tissues 13 and a sling 14, and measure the load the sling places on the flex-beam's sensing region 6, said load being less than the load that the sling will impart on the urethra and periurethral tissues once the sling is positioned and the device is removed. Placing the flex-beam between the periurethral tissues and sling is made easier by the rounded tip 5, which is curved and rounded to slide easily between the sling and tissues.

FIG. 1-D shows the bending load vectors associated with the spacer. In 1-D, the sling is shown pushing as a fulcrum against the curve of the sensing region, imparting Bending Load B compressive force to the bottom 8 of the sensing region, and imparting tensile force to the top 7 of the sensing region 6. Bending Load A consists of load which is placed onto the handle by the surgeon (or gravity alone), a will generate a downward load, and Bending Load C from body tissue manifests on the more distal part of the flex-beam near the tip of the spacer. The spacer may be used as a lever to adjust the sling and to ensure there is at least some slack or decreased tension within the sling once the spacer is removed, while simultaneously being able to measure the loads which the sling places on the spacer. Therefore, several design features are included that enable the loads imparted by the sling onto the spacer to be isolated from other loads generated that could otherwise cause artifacts in the measurements produced from the strain gauges. The gap 9 between the tip 5 and the remainder of the flex-beam 4 isolates the sensing region 6 from being exposed to the loads generated by Bending Load C and thus reduces any artifactual deformation that may occur within the sensing region as a result of Bending Load C.

An alternative embodiment for isolating the loads generated from the sling involves the use of one or more additional sensors (strain gauges, pressure transducer, and the like) near the tip. These sensors (not depicted) can then measure the loads imparted onto the device due to Bending Load C and Bending Load C may then be resolved theoretically and subtracted from Bending Load B in the sensing region.

The sensing region may further comprise grooves (not depicted) which allow wires (not depicted) to connect to the strain gauges and pass into the shaft 2 and then to the display 11.

In one embodiment, the shaft 2 is a steel tube or other metal tube which is flattened to a paddle 10 at the distal end and connects to the flex-beam by mechanical means. As shown in FIGS. 1-A and 1-B, the paddle is positioned at an angle to the shaft, which allows the flex-beam to be correctly positioned while allowing the entire device to be held comfortably and for the sling to be visualized easily. The shaft may be hollow with a wire channel (not depicted), which allows the passage of wires from the flex-beam 4.

The spacer 1 comprises certain electrical components which allow the bending loads to be converted to voltage changes which are output to a display in one or more units which a surgeon can see and then use in his or her decision on much tension to allow between the sling and the tissue. In one embodiment, the display 11 may be located in the handle, and the display may comprise any of several technologies, such as a light emitting diode (LED) display, liquid crystal display (LCD), organic light emitting diode (OLED) display, or other appropriate display. There are buttons 20, located on the handle or at any other convenient location, which allow for the device functions to be executed. These functions include, without limitation, changing display units (e.g. gram-force to Newtons), storing a particular load value, zeroing or blanking the load, or turning the display on/off.

Compressive and tensile strains accumulate on the top and bottom of the sensing region, as depicted in FIG. 1-E and in 2-C and compressive strain and/or tensile strain can be measured. In FIG. 1-E, the strain gauges 17, 18 on the bottom 8 experience compressive strain, as shown by the bending upward of the strain gauges and by the arrows pointing inwardly which symbolize compressive forces on the strain gauge. Likewise, the strain gauges 15, 16 on the top 7 experience tensile strain, as shown by the bending upward of the strain gauges and by the arrows pointing outwardly which symbolize tensile forces on the strain gauge. This deformation is what is readily measured when strain gauges 15-16 and 17-18 are placed onto the top and bottom of the sensing region.

In the embodiment shown in FIGS. 2-A, 2-B and 2-C, a slot 19 is located in the sensing region 6, and the slot accentuates bending when the sling applies force. The slot includes strain gauges which measure the load caused by the sling. The slot 19 may also have built-in one or more stops 25 (columns) that will only allow the sensing region to strain (or bend) to a certain limit. A stop 25 functions to protect the strain gauges from over-straining and to increase the durability of the instrument. In an embodiment in which the handle 3, shaft 2, and flex-beam 4 are produced as a single body, there is also a rounded tip 5 which facilitates easy insertion between the urethra and sling. This embodiment has an angle which allows easier positioning and observation. This embodiment also includes a urethral groove 28 which aids with positioning during sling adjustment. FIG. 2-A shows an embodiment of the spacer with a slot 19 in the sensing region 6. Also shown is the flex-beam 4 and tip 5, the shaft 2, and the handle 3. Section A-A passes through the flex-beam 4 near the center of the sensing region 6 and the slot 19. The shape of the handle in any embodiment can vary widely as long it provides a convenient grip for the surgeon. The shape of the handle is independent of the use of the slot.

The embodiment in FIG. 2-A has only one pair of strain gauges 17, 18 but more can be used, as referenced above.

FIG. 2-B is a cross section taken from points A-A in FIG. 2-A. One pair of strain gauges 17, 18 is depicted at the bottom of the slot 19, along with stops 25 to prevent excessive movement of the strain gauges.

FIG. 2-C shows loading from tensile strain on the bottom strain gauges 17, 18 and from compressive strain on the top strain gauges 15, 16 on the sensing region.

Figure 3:
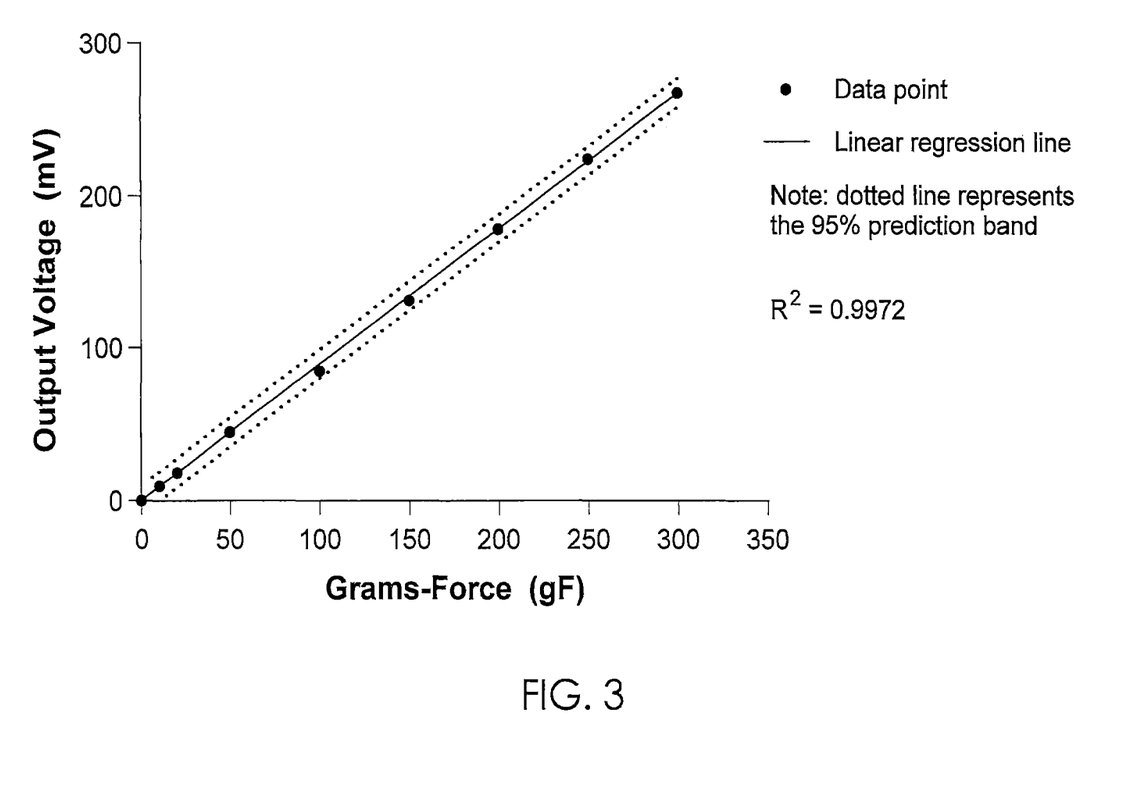
FIG. 3 shows calibration data generated from the spacer showing data from various loads on the sensing region.

FIG. 3 is a graph showing calibration by recording load versus output voltage in a controlled laboratory setting. The spacer was arranged so that a known load, X, was applied to the sensing region 6, and the output voltage under X was recorded. A second, slightly larger load, Y, was then applied and the output voltage under Y was recorded. This process was repeated with continually increasing loads to create a data set indicating output voltages which correspond to increases in load. FIG. 3 records output voltage for 10, 20, 50, 100, 150, 200, 250, and 300 gram-force. This data set created a calibration curve, which is referenced in order to convert output voltage to applied load. In one embodiment this curve is a supplementary data sheet or data file for the clinician to reference. In another embodiment the calibration curve is incorporated into the digital operations of the integrated circuit board, which is contained within the device. The spacer may be manually recalibrated at any later point to insure consistent readings.

Data can be reported in many units including voltage, strain, stress, pressure, and applied force, depending on the mathematical and digital means for processing the output voltage. Bending strain is relatable to bending force, which is directly related to the tension in the sling while the device is being used as a spacer between the sling and paraurethral tissues. A calibration data set, as described earlier, which correlates voltage to applied load, is provided in one embodiment. This load can be output to the display 11 to indicate the load applied by the sling onto the sensing region 6.

Figure 4:
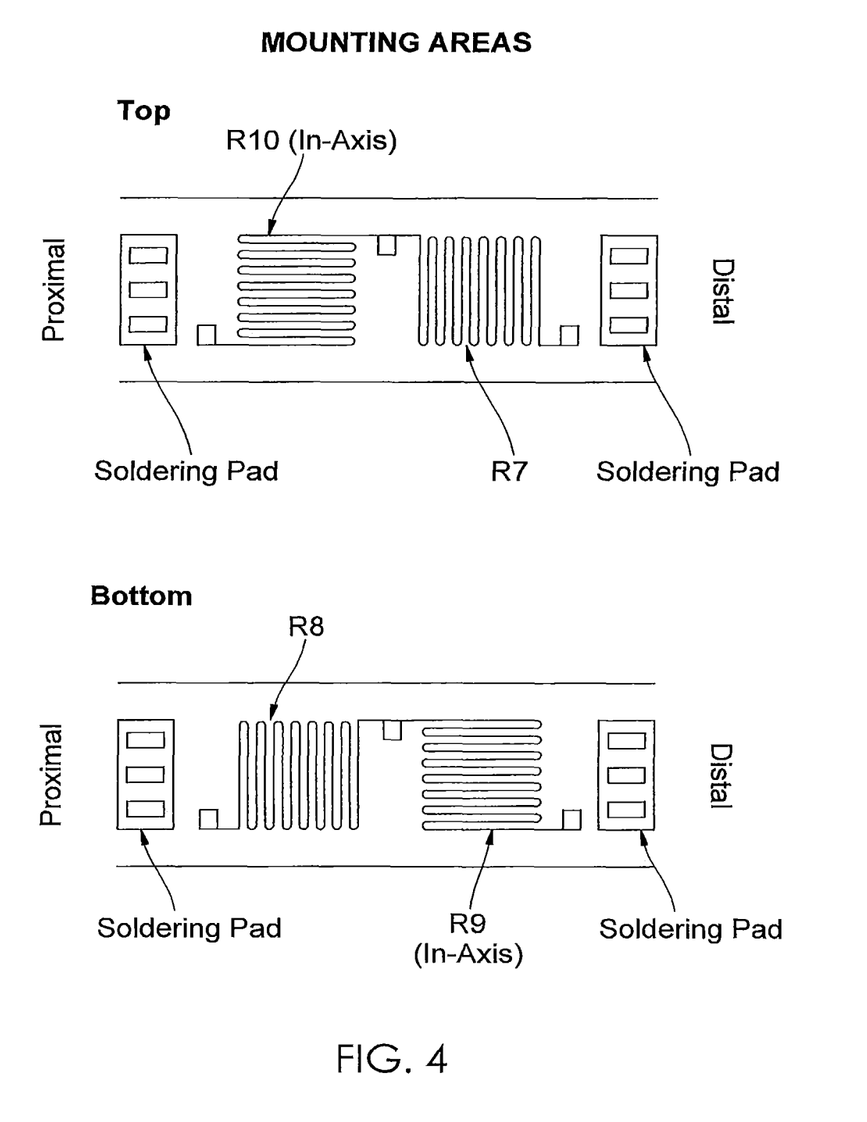
FIG. 4 contains views of the top and bottom of the sensing region showing mounting areas for the strain gauges. Also depicted are the orientations of two pairs of strain gauges, one pair each on the top and the bottom. Each pair comprises one strain gauge aligned along the longitudinal axis of the sensing region (in-axis) and one strain gauge orthogonal to the longitudinal axis (out-of-axis).
Figure 5:
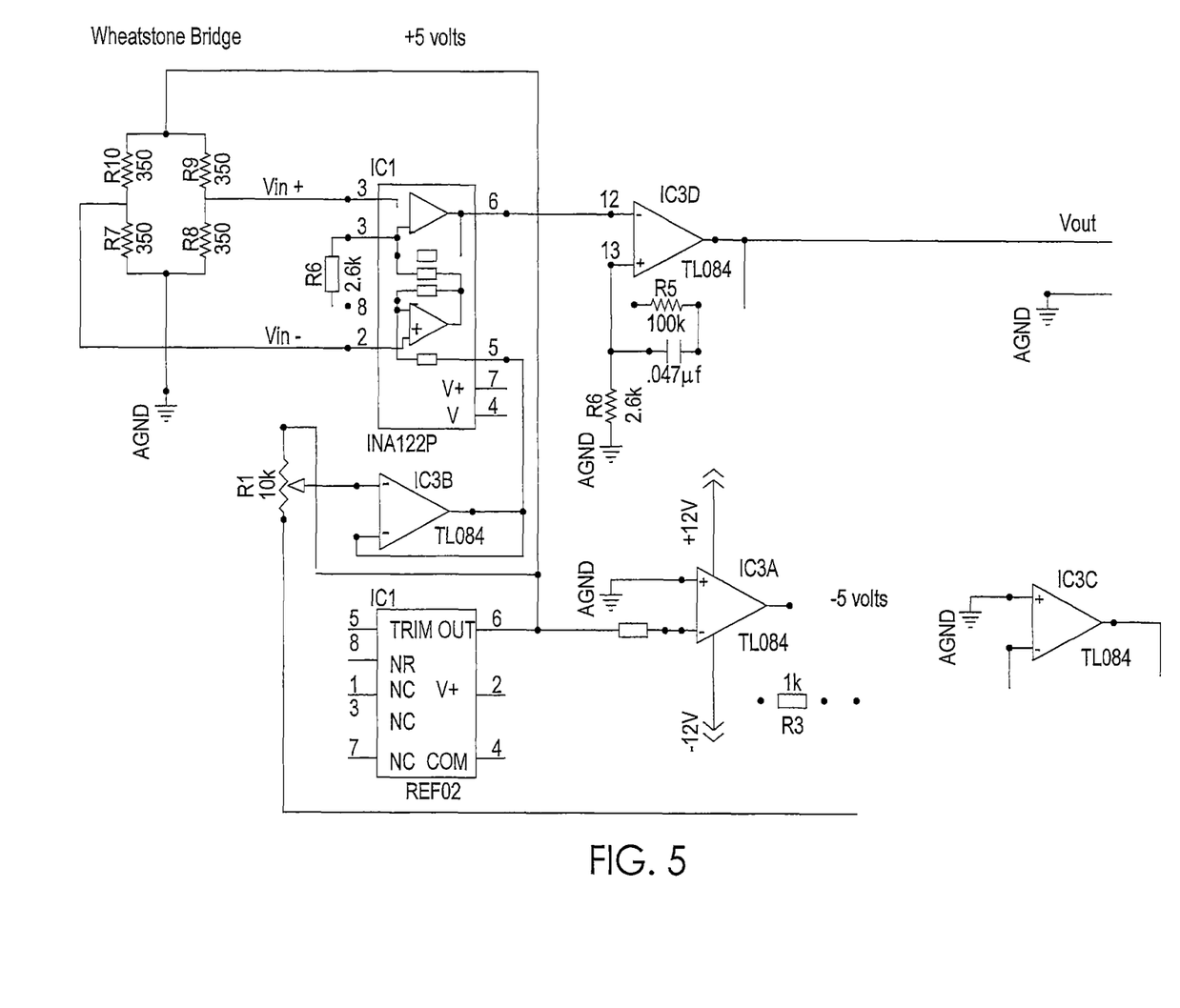
FIG. 5 is the circuit diagram for one embodiment of the spacer.

Although a single strain gauge can be used, one embodiment uses two pairs of strain gauges, that is, four. The embodiment with four strain gauges 15, 16, 17, 18 is represented on FIGS. 4 and 5 showing additional electrical components comprising a strain gauge bridge circuit which communicates with a display 11. An integrated circuit board comprising a microcontroller are used in this embodiment but are not depicted. The foregoing allow measurement of the change in resistance in the strain gauges 15-16, 17-18, convert the change in resistance to a desired loading value such as force, and output that value to the display 11. In FIGS. 4 and 5, strain gauge 15 equals R7, strain gauge 16 equals R10, strain gauge 17 equals R8 and strain gauge 18 equals R9. FIG. 4 is one embodiment of the orientations for a four arm strain gauge bridge (also called a Wheatstone Bridge) with an instrumentation amplifier and power supply. In this embodiment, the bridge consists of two in-axis arms and two out-of-axis arms of 350 ohms each. In this embodiment, the mounting area on the top of the sensing region contains strain gauges R7 and R10 with the in-axis gauge R10 in the proximal end of the top portion of the sensing region and the bottom contains strain gauges R8 and R9 with the in-axis gauge R9 in the distal end of the bottom portion of the sensing region. This offset (orthogonal) in orientation of R7 and R8 (one proximal and one distal) allows capture of as much load as possible from the sensing region. R7 and R8 provide temperature compensation and help reduce the Poisson's effect. An out-of-axis gauge R7, R8 does not register significant change from bending caused by the sling because the out-of-axis gauge because it is not in the direction of the strain which will occur when the sling is loading the sensing region, but it instead functions to register changes in deformation from temperature and/or Poisson's effect. Thus, the changes output from an out-of-axis gauge R7, R8 is presumed to be from increased temperature and/or Poisson's effect, and the Wheatstone Bridge circuit thus adjusts for temperature and/or Poisson's effect.

When force from the sling is imparted onto the sensing region, R9 on the bottom of the sensing region is in compression so resistance decreases causing a voltage increase at the positive input to the amplifier while R10 is in tension, increasing its resistance causing the voltage to decrease at the negative input of the amplifier, as shown on FIG. 5. In one embodiment, this difference in voltage is then amplified approximately by a factor of 828. The input amplifier is an instrumentation amplifier to mitigate common mode noise. The instrumentation amplifier also has an offset pin, as shown on FIG. 5, which is used to zero the output of the instrumentation amplifier. For other embodiments, the circuit diagram can vary depending on the number, placement and resistance of the strain gauges.

In one embodiment, the components comprise a microcontroller (not shown) capable of reading the output voltage and then converting this to load and sending the signal to a display, i.e., a numeric display of any kind (e.g. LCD, LED, etc) and a power supply sufficient to power all of these circuit components. The display settings (e.g. output units of measurement) may be changed using, for example, various buttons 20.

Bending strains and stresses are directly correlated to mechanical load applied to the spacer. One option for reporting the flexural deformation is to solve for the mechanical load theoretically via a shear/bending moment diagram strategy. Since the circuit measures a change in output voltage due to a change in strain gauge resistance from the strain, it is possible to accurately correlate mechanical load to strain via these equations.

Figure 6:
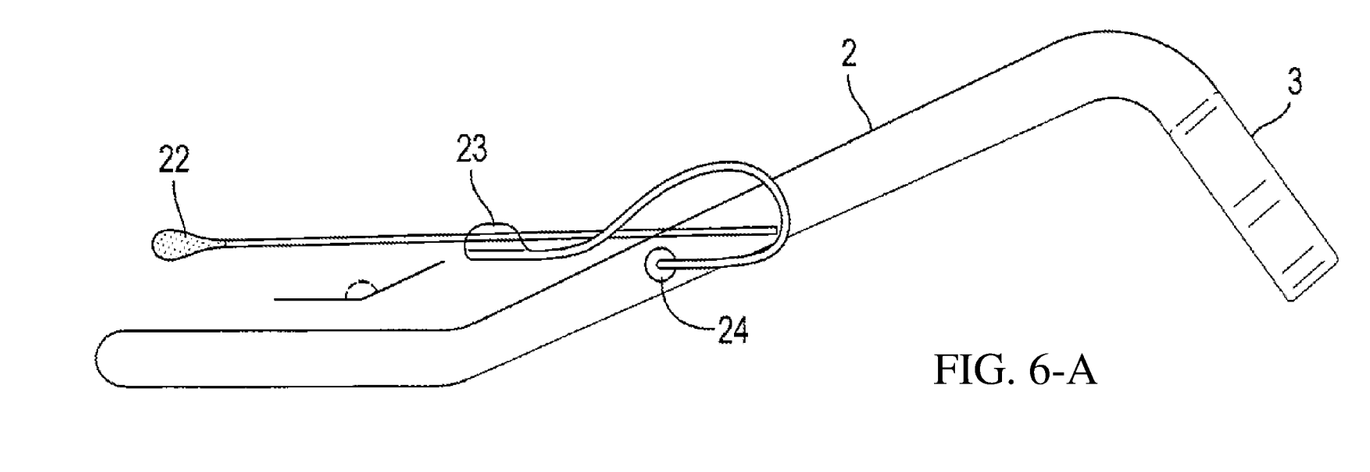

In another embodiment, the spacer comprises all the same features as above, but further comprises an angle sensor 24 which is selected from the group consisting of a potentiometer encoder, gyroscope, accelerometer, a rotary Hall-effect sensor, a magnetoresistive sensor, a resistive sensor, an inductive sensor, and an optical sensor, for quantification of urethral angle and mobility (change in urethral angle during Valsalva maneuver) during sling placement or during office clinical exam. In this embodiment there may be an area between the ends of the instrument that is slightly raised compared to the embodiment without the sensor. Moreover, there may also be a bifurcation 21 in the shaft 2 for a probe holder 23 which communicates with the angle sensor 24. The probe holder 23 has means for attaching a probe 22 consisting of a shaft with a soft tip (in one embodiment a disposable cotton swab) and a probe holder 23 to rotate around a perpendicular shaft 27 connected to a means of measuring angle such as a potentiometer or encoder. The probe holder 23 and probe 22 may swivel around the shaft 27. The bifurcation 21 within the device allows for this swiveling. The probe 22 is gripped by the probe holder via, for example, a snap mechanism which may be a serrated U-shape structure. The degree of rotation around the angle sensor's shaft 27 is directly proportional to changes in electrical properties of its circuit (e.g., voltage, current, impedance).

For quantification of urethral angle or mobility during sling placement, the end of the probe 22 is placed approximately 1.5-3 cm into the urethra. The flex-beam is introduced between the urethra and the sling as previously described. The probe is then snapped into the probe holder 23. The sensor, e.g., a potentiometer, is then reset (or set to zero) via the input buttons 20. The patient is asked to Valsalva (bear down or cough) if the patient is conscious, or a Crede maneuver (manual pressing of the bladder) if the patient is unconscious (can still be done on a conscious patient). As the urethra moves up and down during the Valsalva or Crede maneuver, this movement is transferred to the angle sensor 24 via the probe 22 and probe holder 23. This angular change of the movement is quantified by the angle sensor 24, which transduces the angular change directly into changes in the electrical properties of its circuit (e.g., voltage or current). The relationship between this change in electrical output and angular change can be pre-determined using calibration curve similar to previously described. The urethral mobility angle measurement alone can be used by the surgeon to determine ideal sling placement. The load between the sling and the device alone can be used to determine ideal sling placement. Alternatively, the urethral mobility angle along with the load between the sling and the spacer is used by the surgeon to develop a "sling placement index" that utilizes both values to determine ideal sling placement.

There are a number of variables for the design of the sensing region 6. The material properties of the sensing region directly impact the device function. The stiffness of the material properties affect the range of load values that are accurately read by the device (i.e. stiffer materials will read accurately in a higher range of load values, and less stiff materials will read accurately in a lower range of load values). In one embodiment, the material for the flex-beam 4 and the sensing region 6 is a resilient plastic such as polypropylene or polyethylene. The geometry of the sensing region also impacts device function. For a given material, a thicker sensing region will behave as a stiffer structure than a thinner sensing region. As a result, a thicker sensing region will read more accurately in a higher range of load values and a thinner sensing region will read more accurately in a lower range of load values. Alternative geometries may be used for the sensing region such as a cantilevered beams, or different thickness profiles within the sensing region which serve to concentrate stresses near a strain gauge (i.e. a thinner area near a strain gauge which serves to increase the strain on that strain gauge, thereby increasing the strength of the sensor reading for a given load). These geometries may be selected and altered as a means of optimizing the range of values most accurately read by the surgical device.

The material for the sensing region and any nearby region of the device should be mechanically and thermodynamically elastic in nature, with regards to the level loading indicated for the use of the device. This serves to ensure more consistent readings. A material that behaves in a mechanically or thermodynamically viscous or plastic manner within the loading level indicated for the use of the device would be largely undesirable, as repeated loading cycles could ultimately result in different readings for identical loads. If a material that were chosen that behaves in a mechanically or thermodynamically viscous or plastic manner within the loading level indicated for the use of the device, the sensing components and other aspects of configuration would need to account for this.

The strain gauges can measure the load applied to the sensing region 6 when aligned parallel to the direction strain, and serve as temperature compensating components of a strain gauge bridge when placed perpendicular to the direction of the strain. It is important that the material selected for the sensing region be mechanically isotropic so that the strain gauges sensing strain and the gauges performing temperature compensation are not affected by the unequal effects of mechanical anisotropy. If an anisotropic material is used, it is important that the readings of the sensing region are adjusted to account for the material's anisotropy.

The material and geometric properties of the sensing region 6 and flex-beam 4 will dictate the degree of bending at the sensing region and thus the degree of strain experienced by each strain gauge, and the important parameters revolve around how the device responds to loads, more specifically, the stress-to-strain ratio at the loads applied during surgical sling placement. Therefore, the linear region of the strain versus voltage plot can be tuned by altering the material properties of the sensing region. In addition to material properties, the design of the geometry of the sensing region will also influence the quantity of strain felt by the strain gauges. For example, if the sensing region is very long, then there will be more bending at the middle where the strain gauges are placed. If the sensing region is shortened, then there will be less bending at the middle. All of these properties impact the sensitivity and resolution of the load measurements. For example, if the device's sensing region is made of a very stiff material (e.g. steel) and the slot is fairly short, then a significant amount of load must be applied which will correspond only to a fairly small amount of change in resistance within the strain gauges and the electric circuit. Such a design would not be ideal for the measurement of small loads (i.e. +/−5 grams) with high accuracy and precision, but may be suitable for measuring loads in the kilogram range.

The invention may further comprise an algorithm designed to determine the ideal loads and/or angles for slings based on each patient's specific needs. In this algorithm, a number of patients undergoing sub-urethral sling surgery for SUI may undergo an evaluation of lower urinary tract prior to surgery that may include at least one of the following: q-tip test for urethral hypermobility assessment, evaluation for pelvic organ prolapse, pad tests, bladder diary, force-of-stream evaluation, and/or urodynamic observations. Said urodynamic observations may include measures of bladder sensation during filling cystometry (e.g. volume at first sensation of filling, volume at first desire to void, volume at strong desire to void), measures of detrusor function during filling cystometry (e.g. evidence of detrusor overactivity, etc), measures of bladder compliance during filling cystometry, measures of bladder capacity during filling cystometry, measures of urethral function during filling cystometry (e.g. urethral pressure, urethral pressure profile, maximum urethral closure pressure, functional profile length, pressure transmission ratio, abdominal leak point pressure, detrusor leak point pressure), and/or measures obtained during pressure-flow studies (e.g. urine flow rates, voided volumes, time to maximum flow, premicturition pressures, opening pressures, pressure at maximum flow, etc). During surgery, surgeons would tighten the sub-urethral sling using the spacer. However, surgeons would be blinded to the load they placed on the sling that was measured by the device. Subsequently, patients would undergo follow-up evaluations such as those described previously and/or questionnaires that aim to determine postoperative outcomes. All of these data (including pre-operative lower urinary tract evaluation, sling loads at device interface during surgery, and post-operative outcomes) may then be used to conduct statistical analyses (e.g. logistic regression models, linear regression models, and/or receiver operating characteristic curves, etc) to develop a model that may be used to inform the surgeon of the ideal sling loads to be used for surgery based on patients' pre-operative evaluations. In this method, sling loads used during surgery will be individualized to patients based on pre-operative evaluations.

As can be seen from the above, the invention further comprises a method comprising the steps of: inserting a measuring device between body tissue and a sling, measuring the load on the measuring device from the sling, outputting electrical changes from the load on the measuring device, and reporting the electrical changes such as, for example, voltage changes (or derivatives thereof) to the user.

Also, as seen from the above, the invention further comprises a method comprising the steps of: inserting a probe into a patient's body cavity such as the urethra, inducing movement of the body cavity through the patient's cough or bearing down or manipulation by the surgeon, measuring the movement of the body cavity in response to the previous step, and reporting the electrical changes such as voltage changes (or derivatives thereof) from the previous step.

We claim:

1. A method relating to implantation of a sling into a patient comprising:
   inserting a first end of a spacer into a patient where the spacer has a second distal end external to the patient while the first end of the spacer is inserted into the patient
   attaching a first portion of the sling to a predetermined portion of the first end of the spacer containing a sensor for determining a load applied from the sling to the first end of the spacer;
   attaching a second portion of the sling to a predetermined portion of body tissue of the patient;
   displaying to an operator of the spacer upon a display forming another part of spacer the load applied from the sling to the first end of the spacer; wherein
   the spacer allows the operator to simultaneously quantify the load and adjust a tension of the sling whilst employing the spacer as a spacing tool between the predetermined portion of the bodily tissue of the patient and the sling.

2. The method according to claim 1, wherein
   the first end of the spacer comprises:
      a tip disposed at an end of the first end of the spacer which is inserted into the patient first;
      a flex-beam coupled between the tip and a second distal end of the first end of the spacer; wherein
   the tip is flexibly coupled to the flex-beam via a paddle;
   the flex-beam bends in response to the load applied by the sling; and
   the sensor is disposed within the flex-beam and comprises at least one mechanical load transducer.

3. The method according to claim 2, wherein
   the first end of the spacer further comprises a pin; and
   the pin limits movement of the flex-beam to an axis perpendicular to both the paddle and a longitudinal axis of the first end of the spacer along which the flex-beam and the tip are aligned.

4. The method according to claim 2, wherein
   a lower surface of the flex-beam distal to the paddle is concave; and
   the lower surface of the flex-beam provides the operator with haptic and visual feedback that the sling is located at the right location.

5. The method according to claim 1, wherein
   the sensor comprises at least one mechanical load transducer; and
   the at least one mechanical load transducer is selected from the group consisting of a strain gauge, a standard load transducer, a pressure-sensitive-conductive rubbers and a piezoelectric force transducer.

6. The method according to claim 1, wherein
   the first end of the spacer and the second end of the spacer are each attached to a central portion of the spacer;
   the first end of the spacer is orientated at a first predetermined angle to the central portion of the spacer relative to a longitudinal axis of the central portion of the spacer;
   the second end of the spacer is orientated at a second predetermined angle to the central portion of the spacer relative to the longitudinal axis of the central portion of the spacer; and
   the display is within the second end of the spacer.

7. The method according to claim 1, wherein
   the sensor measures the load applied by the sling to the spacer rather than that the sling exerts on the predetermined portion of the bodily tissue of the patient; and
   the load exerted by the sling upon the predetermined portion of the bodily tissue of the patient when the spacer is removed is lower than the load measured when the spacer is employed.

8. The method according to claim 1, wherein
   the first end of the spacer comprises:
      a tip disposed at an end of the first end of the spacer which is inserted into the patient first;
      a flex-beam coupled between the tip and a second distal end of the first end of the spacer;
      a paddle on one side of the first end of the spacer connecting the tip to the flex-beam; and
      a gap between the tip and the flex-beam; wherein
   the sensor is disposed within the flex-beam and comprises:
      one or more first strain gauges disposed within a first portion of the flex-beam towards the paddle; and
      one or more second strain gauges disposed within a second portion of the flex-beam distal to the paddle; and
   the gap between the first portion of the flex-beam and a second portion of the flex-beam isolating any bending load applied near the tip from the bending load applied to the flex-beam.

9. The method according to claim 8, wherein
   the first end of the spacer further comprises a pin; and
   the pin limits movement of the flex-beam to an axis perpendicular to both the paddle and a longitudinal axis of the first end of the spacer along which the flex-beam and the tip are aligned.

10. The method according to claim 8, wherein
    a lower surface of the flex-beam distal to the paddle is concave; and
    the lower surface of the flex-beam provides the operator with haptic and visual feedback that the sling is located at the right location.

11. A spacer for use in implanting a sling into a patient comprising:
    a first end of the spacer comprising a tip disposed at an end of the first end of the spacer while the spacer is inserted into the patient and a flex-beam coupled between the tip and a distal end of the first end of the spacer, the flex-beam comprising a first sensor for measuring a load applied to the flex-beam by the sling;
    a second end of the spacer comprising an end forming a handle for the spacer and a distal end; and a central portion of the spacer disposed between the distal end of the first end of the spacer and the distal end of the second end of the spacer; wherein the tip is flexibly coupled to the flex-beam;

the flex-beam bends in response to the load applied by the sling.

12. The spacer according to claim 11, wherein the first end of the spacer is orientated at a first predetermined angle to the central portion of the spacer relative to a longitudinal axis of the central portion of the spacer defined by the first end of the spacer and the second end of the spacer;

the second end of the spacer is orientated at a second predetermined angle to the central portion of the spacer relative to the longitudinal axis of the central portion of the spacer; and the end of the second end of the spacer forming the handle comprises at least one of a display for displaying the load applied and one or more buttons.

13. The spacer according to claim 11, further comprising a mounting coupled to the central portion of the spacer for attachment of a probe such that a first end of the probe is disposed above the first end of the spacer;

a second sensor disposed within the central portion of the spacer for determining angular rotation of the probe relative to the spacer; wherein a predetermined portion of the central portion of the spacer is bifurcated allowing a second distal end of the probe to project and move within an opening within the predetermined portion of the central portion of the spacer which is bifurcated.

14. The spacer according to claim 13, wherein the mounting is connected to a pivot disposed at a predetermined position within the predetermined portion of the central portion of the spacer which is bifurcated; and the second sensor measures rotation of the pivot.

15. The spacer according to claim 11, wherein the first end of the spacer further comprises:
  a paddle on one side of the first end of the spacer connecting the tip to the flex-beam; and
  a gap between the tip and the flex-beam; and the first sensor is disposed within the flex-beam and comprises:
  one or more first strain gauges disposed within a first portion of the flex-beam towards the paddle; and
  one or more second strain gauges disposed within a second portion of the flex-beam distal to the paddle; wherein the gap between the first portion of the flex-beam and a second portion of the flex-beam isolates any bending load applied near the tip from the bending load applied to the flex-beam.

16. A method relating to implantation of a sling into a patient comprising:

inserting a first end of a probe into a urethra of the patient;

attaching the probe to a mounting forming part of a spacer wherein angular movement of the probe relative to the spacer is determined in dependence upon an electrical output from a first sensor forming another part of the spacer;

establishing a reference for the probe's angular position relative to the spacer upon establishing an action of a first operator with respect to a user input interface upon the spacer;

performing one of Valsalva maneuver by the patient and a Crede maneuver upon the patient by a second operator;

automatically quantifying an angular change in the probe via a microprocessor forming part of the spacer by converting the electrical output from the first sensor; and determining placement of the sling in dependence upon the quantified angular change.

17. The method according to claim 16, further comprising positioning the probe such that the first end of the probe which is also inserted into the patient is disposed between the urethra and the sling;

connecting the sling to predetermined portion of the first end of the probe containing a second sensor; and determining a load between the sling and the spacer during its implantation in dependence upon an electrical output of the second sensor.

18. The method according to claim 16, further comprising determining with a second sensor forming part of the spacer a load between the sling during its implantation and the spacer employed during the implantation of the sling; and determining placement of the sling is performed by establishing a sling placement index in dependence upon the quantified angular change and the load determined with the spacer between the sling and the spacer.

19. The method according to claim 16, wherein the probe and the mounting rotate around an axis perpendicular to a longitudinal axis of the spacer.

20. The method according to claim 16, wherein the spacer comprises a first end for insertion into the patient and a second end external to the patient;

the first end of the probe is disposed towards the first end of the spacer;

the mounting is disposed between the first end of the spacer and the second end of the spacer;

a portion of the body of the spacer between the mounting and the second end of the spacer is a bifurcated portion allowing a second distal end of the probe to project and move within an opening within the spacer formed by the bifurcated portion of the spacer.

21. The method according to claim 16, wherein the spacer comprises a first end for insertion into the patient disposed at a first angular offset relative to a central portion of the spacer and a second end external to the patient disposed at a second angular offset relative to the central portion of the spacer;

the first end of the probe is disposed towards and above the first end of the spacer;

the mounting is disposed above at least one of the central portion and the first end of the spacer;

the central portion of the spacer comprises a bifurcated section allowing a second distal end of the probe to project and move within an opening within the spacer formed by the bifurcated section; and the mounting is connected to a pivot disposed at a predetermined position within the bifurcated section.

22. The method according to claim 16, wherein the spacer comprises a first end for insertion into the patient disposed at a first angular offset relative to a central portion of the spacer and a second end external to the patient disposed at a second angular offset relative to the central portion of the spacer.

* * * * *